(12) United States Patent
Jensen et al.

(10) Patent No.: US 8,358,128 B2
(45) Date of Patent: *Jan. 22, 2013

(54) SURGICAL NAVIGATION SYSTEM WITH MAGNETORESISTANCE SENSORS

(75) Inventors: Vernon Thomas Jensen, Draper, UT (US); William H. Huber, Scotia, NY (US)

(73) Assignee: General Electric Company, Schnectady, NY (US)

( * ) Notice: Subject to any disclaimer, the term of this patent is extended or adjusted under 35 U.S.C. 154(b) by 451 days.

This patent is subject to a terminal disclaimer.

(21) Appl. No.: 12/325,123

(22) Filed: Nov. 28, 2008

(65) Prior Publication Data

US 2010/0137705 A1    Jun. 3, 2010

(51) Int. Cl.
G01R 33/09    (2006.01)
A61B 5/05    (2006.01)

(52) U.S. Cl. .............. 324/252; 324/207.21; 600/424

(58) Field of Classification Search ............ 324/207.21, 324/252; 338/32 R; 600/424
See application file for complete search history.

(56) References Cited

U.S. PATENT DOCUMENTS

| | | | |
|---|---|---|---|
| 5,422,621 A * | 6/1995 | Gambino et al. | ........... 338/32 R |
| 5,729,129 A | 3/1998 | Acker | |
| 5,752,513 A | 5/1998 | Acker et al. | |
| 5,782,765 A | 7/1998 | Jonkman | |
| 5,818,323 A * | 10/1998 | Maeda et al. | ............... 338/32 R |
| 6,172,499 B1 | 1/2001 | Ashe | |
| 6,211,666 B1 * | 4/2001 | Acker | ...................... 324/207.17 |
| 6,241,671 B1 | 6/2001 | Ritter et al. | |
| 6,246,231 B1 | 6/2001 | Ashe | |
| 6,427,079 B1 | 7/2002 | Schneider et al. | |
| 6,493,573 B1 | 12/2002 | Martinelli et al. | |
| 6,528,991 B2 | 3/2003 | Ashe | |
| 6,610,602 B2 * | 8/2003 | Gambino et al. | ............. 438/689 |
| 6,636,757 B1 | 10/2003 | Jascob et al. | |
| 6,642,714 B2 * | 11/2003 | Kobayashi et al. | ........... 324/252 |
| 6,690,963 B2 * | 2/2004 | Ben-Haim et al. | ............ 600/424 |
| 6,701,179 B1 | 3/2004 | Martinelli et al. | |
| 6,784,660 B2 | 8/2004 | Ashe | |
| 6,789,043 B1 | 9/2004 | Nelson et al. | |
| 6,812,842 B2 | 11/2004 | Dimmer | |
| 6,822,570 B2 | 11/2004 | Dimmer et al. | |
| 6,838,990 B2 | 1/2005 | Dimmer | |
| 6,856,823 B2 | 2/2005 | Ashe | |
| 7,174,202 B2 * | 2/2007 | Bladen et al. | ................. 600/424 |
| 7,176,798 B2 | 2/2007 | Dimmer et al. | |
| 7,324,915 B2 * | 1/2008 | Altmann et al. | .............. 702/150 |
| 7,373,271 B1 | 5/2008 | Schneider | |
| 7,402,996 B2 | 7/2008 | Arai et al. | |
| 7,683,612 B2 * | 3/2010 | Koyama | ........................ 324/249 |
| 2003/0011359 A1 | 1/2003 | Ashe | |
| 2003/0173953 A1 | 9/2003 | Ashe | |
| 2003/0233042 A1 | 12/2003 | Ashe | |
| 2005/0245821 A1 | 11/2005 | Govari et al. | |

(Continued)

FOREIGN PATENT DOCUMENTS

EP    42707    12/1981

(Continued)

Primary Examiner — Bot Ledynh

(57) ABSTRACT

A surgical navigation system having one or more magnetoresistance sensors, where the sensors have the noise and dynamic range appropriate for electromagnetic position and orientation tracking. The surgical navigation system comprising at least one magnetoresistance reference sensor rigidly attached to an anatomical reference of a patient, at least one magnetoresistance sensor attached to at least one device, and at least one processor for determining the position and orientation of the at least one device.

13 Claims, 6 Drawing Sheets

U.S. PATENT DOCUMENTS

| | | |
|---|---|---|
| 2005/0261566 A1 | 11/2005 | Hanley |
| 2007/0078334 A1 | 4/2007 | Scully et al. |
| 2008/0001756 A1 | 1/2008 | Dimmer et al. |
| 2008/0269596 A1 | 10/2008 | Revie et al. |
| 2009/0058413 A1* | 3/2009 | Kraemer et al. ............ 324/252 |
| 2010/0137705 A1* | 6/2010 | Jensen et al. ............... 600/424 |
| 2010/0138183 A1* | 6/2010 | Jensen et al. ............... 702/150 |
| 2010/0249571 A1* | 9/2010 | Jensen et al. ............... 600/409 |

FOREIGN PATENT DOCUMENTS

| | | |
|---|---|---|
| JP | 2002365010 | 12/2002 |
| WO | WO9732179 | 9/1997 |
| WO | WO9960370 | 11/1999 |

\* cited by examiner

SURGICAL NAVIGATION SYSTEM WITH MAGNETORESISTANCE SENSORS

BACKGROUND OF THE INVENTION

This disclosure relates generally to surgical navigation systems, and more particularly to a surgical navigation system utilizing magnetoresistance sensors.

Surgical navigation systems track the precise position and orientation of surgical instruments, implants or other medical devices in relation to multidimensional images of a patient's anatomy. Additionally, surgical navigation systems use visualization tools to provide the surgeon with co-registered views of these surgical instruments, implants or other medical devices with the patient's anatomy.

The multidimensional images may be generated either prior to or during the surgical procedure. For example, any suitable medical imaging technique, such as X-ray, computed tomography (CT), magnetic resonance (MR), positron emission tomography (PET), ultrasound, or any other suitable imaging technique, as well as any combinations thereof may be utilized. After registering the multidimensional images to the position and orientation of the patient, or to the position and orientation of an anatomical feature or region of interest, the combination of the multidimensional images with graphical representations of the navigated surgical instruments, implants or other medical devices provides position and orientation information that allows a medical practitioner to manipulate the surgical instruments, implants or other medical devices to desired positions and orientations.

Current surgical navigation systems that include position and orientation sensors, or sensing sub-systems based on electromagnetic (EM), radio frequency (RF), optical (line-of-sight), and/or mechanical technology.

EM sensors are typically implemented with coils or microcoils to generate and detect the magnetic fields. While coil based EM sensors have been successfully implemented, they suffer from poor signal-to-noise ratio (SNR) as the transmitter coil frequency is reduced and/or the receiver coil volume is reduced. Reducing the SNR translates into a reduced range (distance from transmitter to receiver) of the EM sensors that may result in a clinically meaningful position error.

Another problem associated with coil based EM sensors is that they are susceptible to magnetic field distortions that arise from eddy currents in nearby conducting objects. The tracking technique used with coil based EM sensors relies on a stable magnetic field, or a known magnetic field map. Therefore, unpredictable disturbances resulting from metallic objects in the magnetic field reduce the accuracy or may even render the tracking technique useless. Selecting a magnetic field frequency as low as the application allows reduces problems resulting from eddy currents, however it also reduces the sensitivity of coil based EM sensors since these are based on induction.

Other problems associated with coil based EM sensors is that they are generally more difficult and expensive to manufacture and are also inherently sensitive to parasitic inductance and capacitance from the cables, connectors and electronics because the sensor signal is proportionally smaller while the parasitic signal remains the same. While some of the parasitic contributions may be partially nulled out using more expensive components and manufacturing processes, the remaining parasitic inductance and capacitance result in a reduced range.

In addition to coil based EM sensors, there are a large variety of magnetic sensors with differing price and performance attributes. Hall effect-sensors are typically used to detect fields down to approximately $10^{-6}$ Tesla. These sensors are stable, compact, relatively inexpensive and have a large dynamic range. Anisotropic magnetoresistive (AMR) sensors can detect fields down to approximately $10^{-9}$ Tesla While these sensors are compact and relatively inexpensive, they are highly prone to drift and have a small dynamic range. Therefore AMR sensors need to be reinitialized frequently using high current pulses. Fluxgate magnetometers can detect fields down to approximately $10^{-11}$ Tesla. However these sensors are expensive, bulky and have a relatively small dynamic range. SQUID magnetometers can detect fields down to approximately $10^{-15}$ Tesla. They are also expensive with significant operating costs since they require cryogens or a high-power closed-cycle cooling system.

Therefore, there is a need for a surgical navigation system that includes magnetoresistance sensors having a small form factor, excellent signal-to-noise ratio, excellent low frequency operation, lower sensitivity to parasitic inductance and capacitance, lower sensitivity to distortion, and are very low cost to manufacture.

BRIEF DESCRIPTION OF THE INVENTION

In accordance with an aspect of the disclosure, a surgical navigation system comprising at least one magnetoresistance reference sensor rigidly attached to an anatomical reference of a patient; at least one magnetoresistance sensor attached to at least one device; and at least one processor for determining the position and orientation of the at least one device.

In accordance with an aspect of the disclosure, a surgical navigation system comprising at least one magnetoresistance reference sensor rigidly attached to an anatomical reference of a patient; at least one electromagnetic coil sensor attached to at least one device; and at least one processor for determining the position and orientation of the at least one device.

In accordance with an aspect of the disclosure, a surgical navigation system comprising at least one electromagnetic coil sensor rigidly attached to an anatomical reference of a patient; at least one magnetoresistance sensor attached to at least one device; and at least one processor for determining the position and orientation of the at least one device.

In accordance with an aspect of the disclosure, a surgical navigation system comprising at least one magnetoresistance reference sensor attached to an anatomical reference of a patient; at least one magnetoresistance sensor attached to a first device; at least one optical sensor attached to a second device; and at least one processor for determining the position and orientation of the first device and a second device.

Various other features, aspects, and advantages will be made apparent to those skilled in the art from the accompanying drawings and detailed description thereof

DETAILED DESCRIPTION OF THE INVENTION

Figure 1:
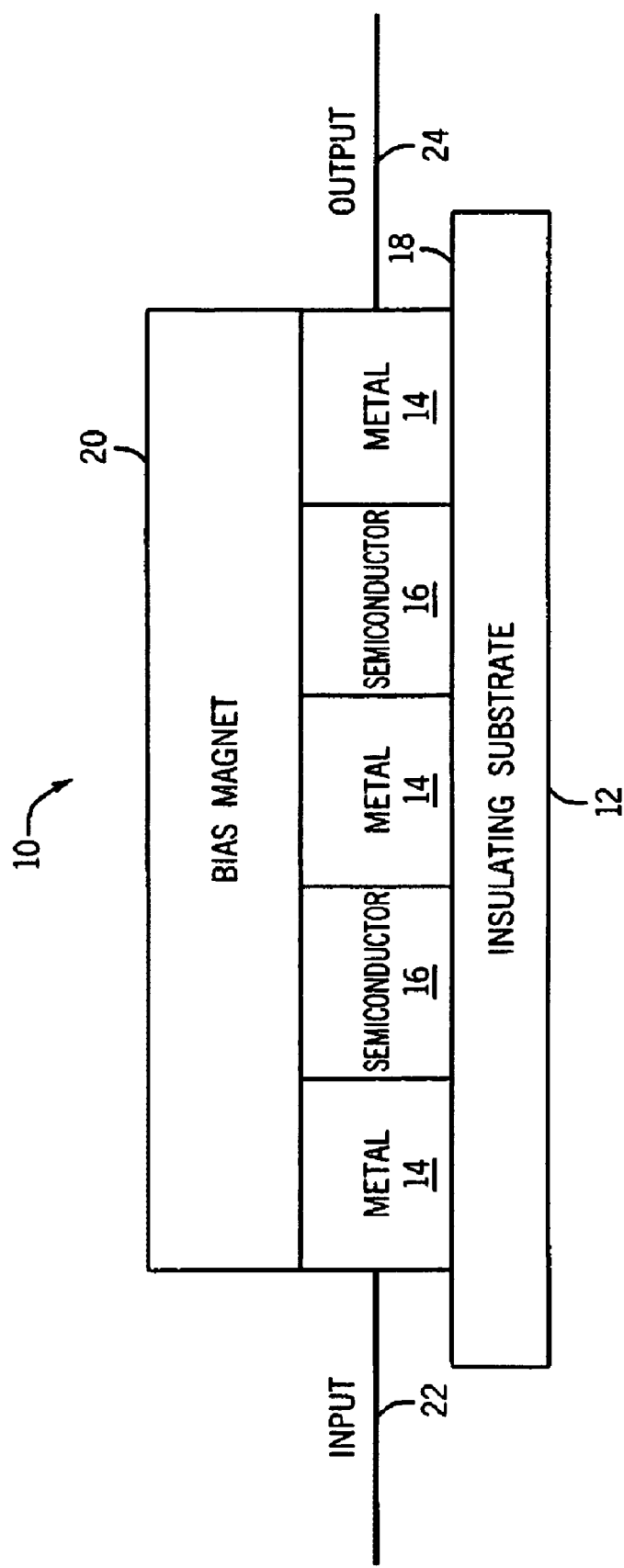
FIG. 1 is an enlarged side view of an exemplary embodiment of a magnetoresistance sensor.

Referring now to the drawings, FIG. 1 illustrates an enlarged side view of an exemplary embodiment of a magnetoresistance sensor 10. A magnetoresistance device is a device that provides a change in electrical resistance of a conductor or semiconductor when a magnetic field is applied. The device's resistance depends upon the magnetic field applied. As shown in FIG. 1, the a magnetoresistance sensor 10 comprises an insulating substrate 12, an alternating pattern of a metal material 14 and a semiconductor material 16 deposited on a surface 18 of the insulating substrate, and a bias magnet material 20 deposited over the alternating pattern of metal material 14 and semiconductor material 16. The alternating pattern of metal material 14 and semiconductor material 16 creates a composite structure with alternating bands of metal material 14 and semiconductor material 16. At least one input connection contact 22 is coupled to the metal material 14 and at least one output connection contact 24 is coupled to the metal material 14.

The semiconductor material 16 may be series connected to increase the magnetoresistance sensor 10 resistance. In an exemplary embodiment, the semiconductor material 16 may be comprised of a single semiconductor element. The bias magnet material 20 subjects the semiconductor material 16 to a magnetic field required to achieve required sensitivity. The magnetoresistance sensor 10 provides a signal in response to the strength and direction of a magnetic field. In an exemplary embodiment, the magnetic field may be approximately 0.1 to 0.2 Tesla.

The application of a magnetic field confines the electrons to the semiconductor material 16, resulting in an increased path length. Increasing the path length, increases the sensitivity of the magnetoresistance sensor 10. The magnetic field also increases the resistance of the magnetoresistance sensor 10. In the geometry disclosed in FIG. 1, at a zero magnetic field, the current density is uniform throughout the magnetoresistance sensor 10. At a high magnetic field, the electrons (or holes) propagate radially outward toward the corners of the semiconductor material 16, resulting in a large magnetoresistance (high resistance).

Many new clinical applications include tracking of a variety of devices including catheters, guidewires, and other endovascular instruments that require sensors to be very small in size (millimeter dimensions or smaller). The active area of the magnetoresistance sensor 10 may be scaled to sizes less than 0.1 mm×0.1 mm.

In an exemplary embodiment, the magnetoresistance sensor may be built with various architectures and geometries, including, giant magnetoresistance (GMR) sensors, and extraordinary magnetoresistance (EMR) sensors.

The magnetoresistance sensor 10 provides a very small form factor, excellent signal-to-noise ratio (low noise operation), and excellent low frequency response. Low noise combined with wide dynamic range enables the magnetoresistance sensor 10 to be used for position and orientation tracking in surgical navigation systems. The low frequency response of the magnetoresistance sensor 10 allows a surgical navigation system to operate at very low frequencies where metal tolerance is maximized.

Figure 2:
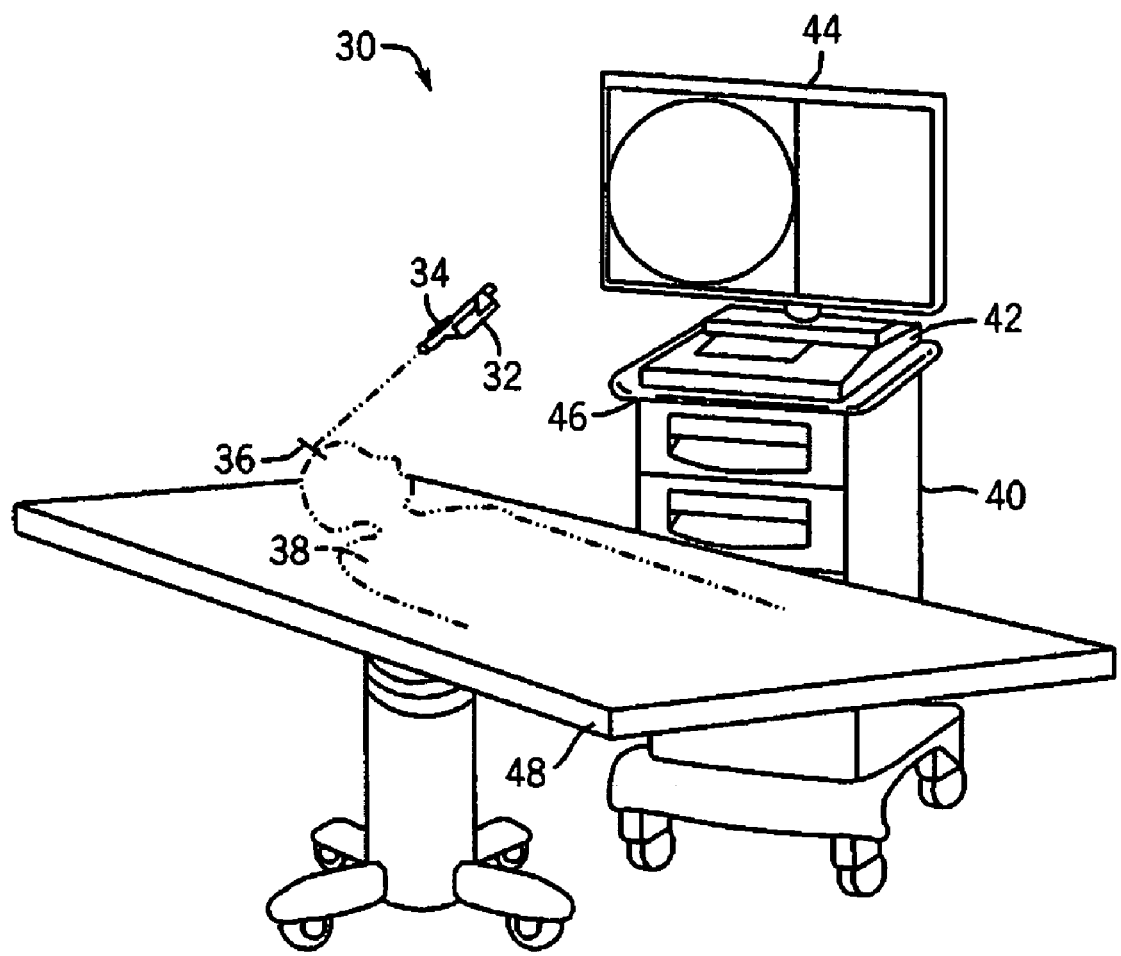
FIG. 2 is a schematic diagram of an exemplary embodiment of a surgical navigation system.

FIG. 2 illustrates a schematic diagram of an exemplary embodiment of a surgical navigation system 30. The surgical navigation system 30 includes at least one magnetoresistance sensor 32 attached to the at least one device 34, and at least one magnetoresistance reference sensor 36 rigidly attached to an anatomical reference of a patient 38 undergoing a medical procedure, and a portable workstation 40. The at least one magnetoresistance reference sensor 36 may also be referred to as a dynamic reference because it is rigidly attached to an anatomical reference of the patient 38 moves along with the patient 38. The portable workstation 40 includes a computer 42, at least one display 44, and a navigation interface 46. The surgical navigation system 30 is configured to operate with the at least one magnetoresistance sensor 32 and the at least one magnetoresistance reference sensor 36 to determine the position and orientation of the at least one device 34. A table 48 is positioned near the portable workstation 40 to support the patient 38 during the medical procedure.

The at least one magnetoresistance sensor 32 may be used to determine one dimension or multiple dimensions of position and/or orientation information (x, y, z, roll, pitch, yaw) relative to the at least one magnetoresistance reference sensor 34, or relative to one or more magnetoresistance sensor 32.

The at least one magnetoresistance sensor 32 and at least one magnetoresistance reference sensor 36 are coupled to the navigation interface 46. The at least one magnetoresistance sensor 32 and the at least one magnetoresistance reference sensor 36 may be coupled to and communicate to the navigation interface 46 through either a wired or wireless connection. The navigation interface is coupled to the computer 42.

The at least one magnetoresistance reference sensor 36 communicates with and receives data from the at least one magnetoresistance sensor 32. The navigation interface 46 is coupled to and receives data from the at least one magnetoresistance reference sensor 36 and the at least one of magnetoresistance sensor 32. The surgical navigation system 30 provides the ability to track and display the position and orientation of multiple devices 34 having magnetoresistance sensors 32 attached thereto.

In an exemplary embodiment, the at least one magnetoresistance sensor 32 may be configured as a transmitter or magnetic field generator, and the at least one magnetoresistance reference sensor 36 may be configured as a magnetic field receiver. It should, however, be appreciated that according to alternate embodiments the at least one magnetoresistance sensor 32 may be configured as a magnetic field receiver, and the at least one magnetoresistance reference sensor 36 may be configured as a magnetic field generator.

In an exemplary embodiment, the at least one magnetoresistance reference sensor 36 generates at least one magnetic field that is detected by at least one magnetoresistance sensor 32. In an exemplary embodiment, the at least one magnetoresistance sensor 32 generates at least one magnetic field that is detected by at least one magnetoresistance reference sensor 36.

The magnetic field measurements may be used to calculate the position and orientation of the at least one device 34 according to any suitable method or system. After the magnetic field measurements are digitized using electronics coupled to the at least one magnetoresistance sensor 32, the digitized signals are transmitted from the at least one magnetoresistance sensor 32 to the navigation interface 46. The digitized signals may be transmitted from the at least one magnetoresistance sensor 32 to the navigation interface 46 using wired or wireless communication protocols and interfaces. The digitized signals received by the navigation interface 46 represent magnetic field information detected by the at least one magnetoresistance sensor 32.

In an exemplary embodiment, the digitized signals received by the navigation interface 46 represent magnetic field information from the at least one magnetoresistance reference sensor 34 detected by the at least one or at least one magnetoresistance sensor 32. The navigation interface 46 transfers the digitized signals to the computer 42. The computer 42 calculates position and orientation information of the at least one device 34 based on the received digitized signals.

The position and orientation information may be transmitted from the computer 42 to the display 44 for review by a medical practitioner.

The surgical navigation system 30 described herein is capable of tracking many different types of devices during different procedures. Depending on the procedure, the at least one device 34 may be a surgical instrument (e.g., an imaging catheter, a diagnostic catheter, a therapeutic catheter, a guidewire, a debrider, an aspirator, a handle, a guide, etc.), a surgical implant (eg., an artificial disk, a bone screw, a shunt, a pedicle screw, a plate, an intramedullary rod, etc.), or some other device. Depending on the context of the usage of the surgical navigation system 30, any number of suitable devices may be used. In an exemplary embodiment, there may be more than one device 34, and more than one magnetoresistance sensor 32 attached to each device 34.

An exemplary system for implementing the computer 42 may include a general purpose computing device including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

Figure 3:
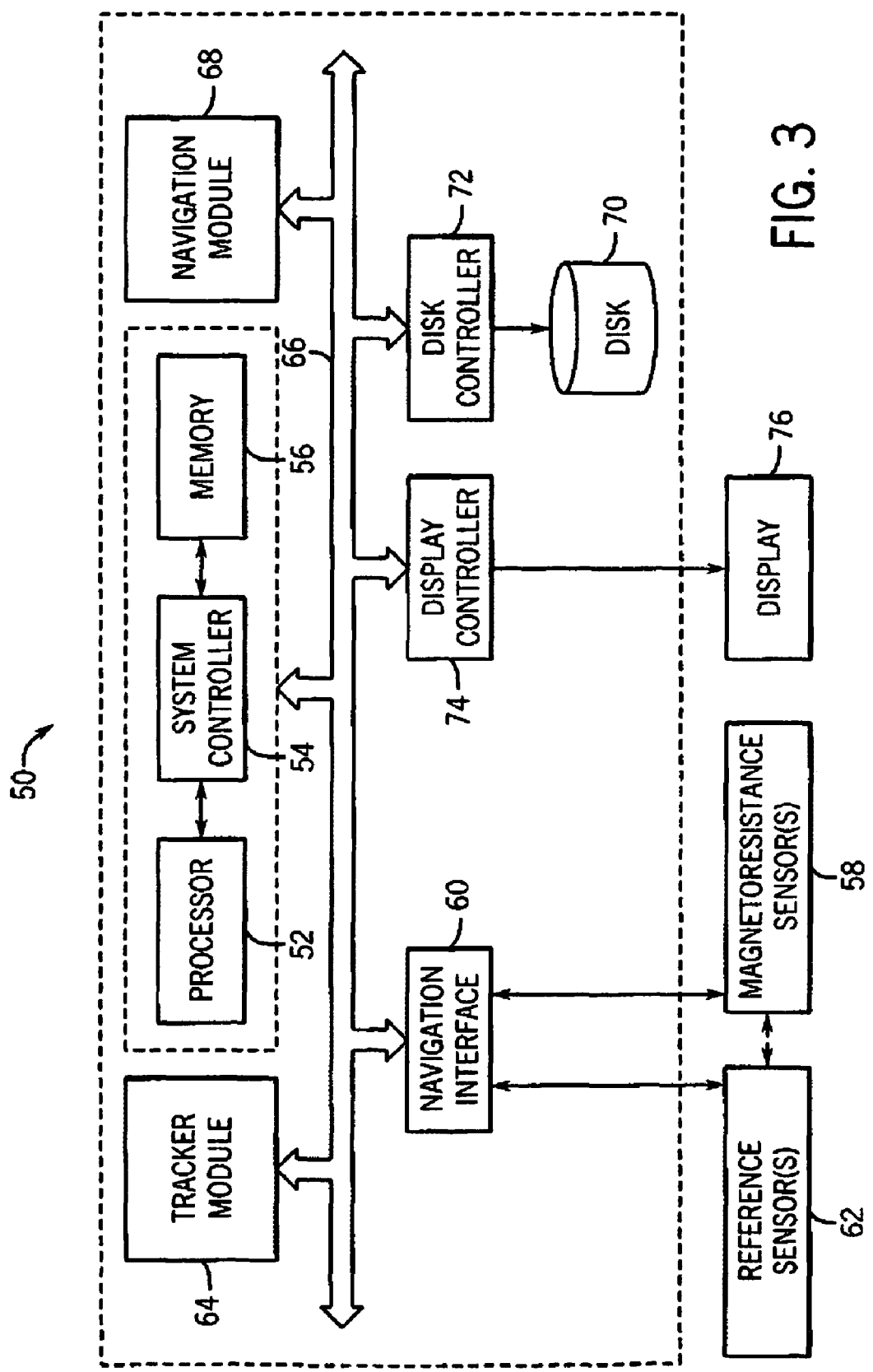
FIG. 3 is a block diagram of an exemplary embodiment of a surgical navigation system.

FIG. 3 illustrates a block diagram of an exemplary embodiment of a surgical navigation system 50. The surgical navigation system 50 is illustrated conceptually as a collection of modules, but may be implemented using any combination of dedicated hardware boards, digital signal processors, field programmable gate arrays, and processors. Alternatively, the modules may be implemented using an off-the-shelf computer with a single processor or multiple processors, with the functional operations distributed between the processors. As an example, it may be desirable to have a dedicated processor for position and orientation calculations as well as a dedicated processor for visualization operations. As a further option, the modules may be implemented using a hybrid configuration in which certain modular functions are performed using dedicated hardware, while the remaining modular functions are performed using an off-the-shelf computer. In the embodiment shown in FIG. 3, the system 50 includes a processor 52, a system controller 54 and memory 56. The operations of the modules may be controlled by the system controller 54.

At least one magnetoresistance sensor 58 and at least one magnetoresistance reference sensor 62 are coupled to a navigation interface 60. The surgical navigation system 50 may be configured to assign a unique identifier to each magnetoresistance sensor 58 and each magnetoresistance reference sensor 62 through the navigation interface 60, so that the surgical navigation system 50 can identify which magnetoresistance sensor is attached to which device, or which magnetoresistance reference sensor 62 is attached to which anatomical reference. In an exemplary embodiment, the at least one magnetoresistance sensor 58 generates at least one magnetic field that is detected by the at least one magnetoresistance reference sensor 62. In an exemplary embodiment, the at least one magnetoresistance reference sensor 62 generates at least one magnetic field that is detected by the at least one magnetoresistance sensor 58.

In an exemplary embodiment, the at least one magnetoresistance sensor 58 may be configured as a transmitter or magnetic field generator, and the at least one magnetoresistance reference sensor 62 may be configured as a magnetic field receiver. It should, however, be appreciated that according to alternate embodiments the at least one magnetoresistance sensor 58 may be configured as a magnetic field receiver, and the at least one magnetoresistance reference sensor 62 may be configured as a magnetic field generator.

The navigation interface 60 receives and/or transmits digitized signals from the at least one magnetoresistance sensor 58 or the at least one magnetoresistance reference sensor 62. The navigation interface 60 may include at least one Ethernet port. The at least one port may be provided, for example, with an Ethernet network interface card or adapter. However, according to various alternate embodiments, the digitized signals may be transmitted from the at least one magnetoresistance sensor 58 or the at least one magnetoresistance reference sensor 62 to the navigation interface 60 using alternative wired or wireless communication protocols and interfaces.

The digitized signals received by the navigation interface 60 represent magnetic field information from the at least one magnetoresistance sensor 58 detected by the at least one magnetoresistance reference sensor 62. In an alternative embodiment, the digitized signals received by the navigation interface 60 represent magnetic field information from the at least one magnetoresistance reference sensor 62 detected by the at least one magnetoresistance sensor 58. The navigation interface 60 transmits the digitized signals to a tracker module 64 over a local interface 66. In an exemplary embodiment, the local interface 66 is a peripheral component interconnect (PCI) bus. However, according to various alternate embodiments, equivalent bus technologies may be substituted. In an exemplary embodiment, the tracker module 64 calculates position and orientation information based on the received digitized signals. This position and orientation information provides a location of a device. The tracker module 64 communicates the position and orientation information to a navigation module 68 over the local interface 66.

Upon receiving the position and orientation information, the navigation module 68 is used to register the location of the device to acquired patient data. In the embodiment illustrated in FIG. 3, the acquired patient data is stored on a disk 70. The acquired patient data may include computed tomography (CT) data, magnetic resonance (MR) data, positron emission tomography (PET) data, ultrasound data, x-ray data, or any other suitable data, as well as any combinations thereof. By way of example only, the disk 70 is a hard disk drive, but other suitable storage devices may be used.

The acquired patient data is loaded into memory 56 from the disk 70. The acquired patient data is retrieved from the disk 70 by a disk controller 72. The navigation module 68 reads from memory 56 the acquired patient data. The navigation module 68 registers the location of the device to acquired patient data, and generates image data suitable to visualize the patient image data and a representation of the device. In the embodiment illustrated in FIG. 3, the image data is transmitted to a display controller 74 over the local interface 66. The display controller 74 is used to output the image data to a display 76.

Various display configurations may be used to improve operating room ergonomics, display different views, or display information to personnel at various locations. For example, as illustrated in FIG. 2, at least one display 44 may be included with the surgical navigation system 30. The at least one display 44 may include two or more separate displays or a large display that may be partitioned into two or more display areas. Alternatively, the at least one display 44 may be mounted on a surgical boom extending from a ceiling or wall of an operating room. The surgical boom may be mounted to and extend from a ceiling or wall of an operating room, attachable to a surgical table, or mounted on a portable cart.

Figure 4:
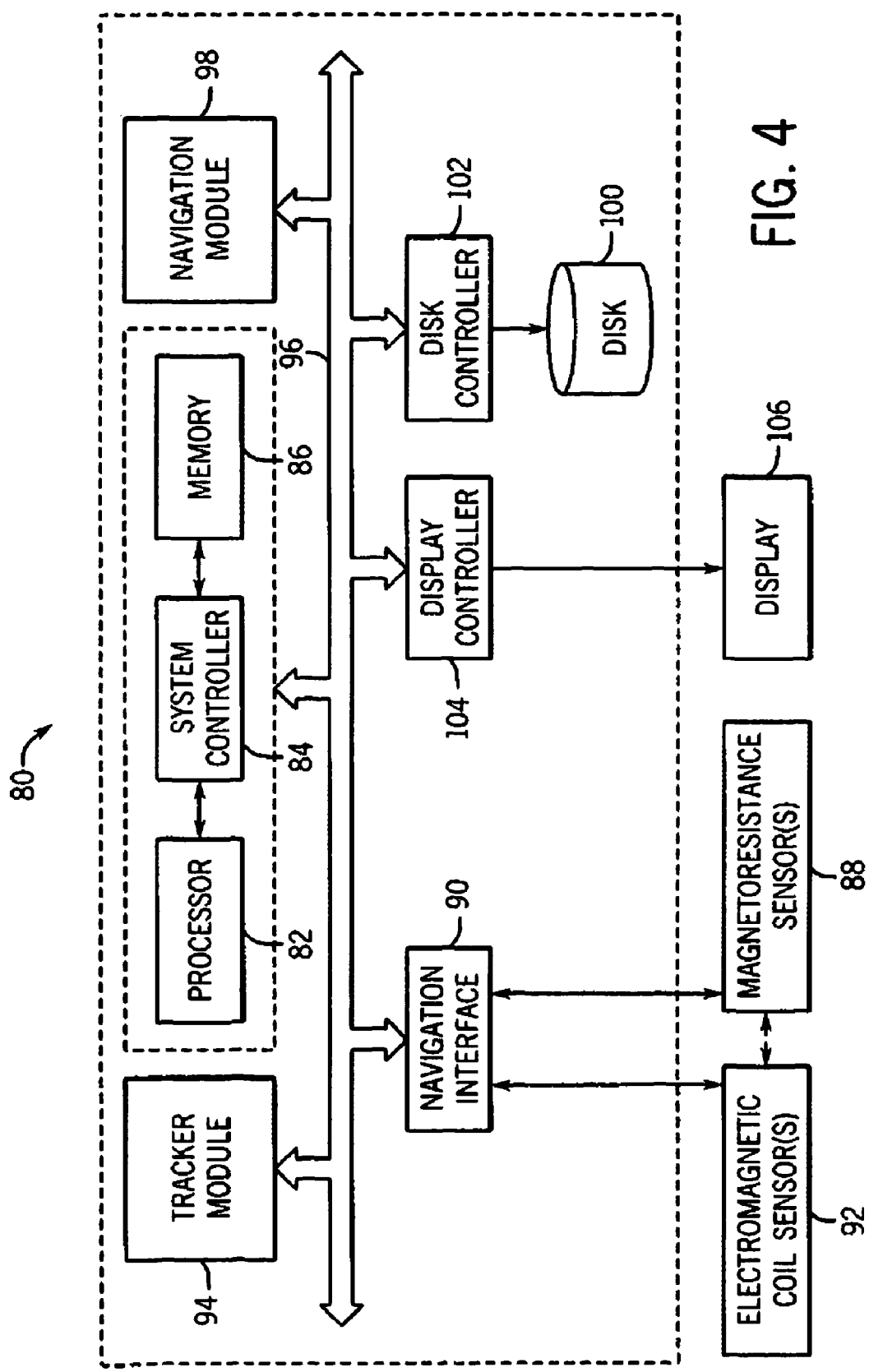
FIG. 4 is a block diagram of an exemplary embodiment of a surgical navigation system utilizing both electromagnetic coil sensor and magnetoresistance sensor technologies.

FIG. 4 illustrates a block diagram of an exemplary embodiment of a surgical navigation system 80. The surgical navigation system 80 is a hybrid surgical navigation system implementing both electromagnetic (EM) coil sensor and magnetoresistance sensor technologies. The surgical navigation system 80 is illustrated conceptually as a collection of modules, but may be implemented using any combination of dedicated hardware boards, digital signal processors, field programmable gate arrays, and processors. Alternatively, the modules may be implemented using an off-the-shelf computer with a single processor or multiple processors, with the functional operations distributed between the processors. As an example, it may be desirable to have a dedicated processor for position and orientation calculations as well as a dedicated processor for visualization operations. As a further option, the modules may be implemented using a hybrid configuration in which certain modular functions are performed using dedicated hardware, while the remaining modular functions are performed using an off-the-shelf computer. In the embodiment shown in FIG. 4, the system 50 includes a processor 82, a system controller 84 and memory 86. The operations of the modules may be controlled by the system controller 84.

At least one magnetoresistance sensor 88 and at least one EM coil sensor 92 are coupled to a navigation interface 90.

In an exemplary embodiment, the at least one magnetoresistance sensor 88 generates at least one magnetic field that is detected by the at least one EM coil sensor 92. In an exemplary embodiment, the at least one EM coil sensor 92 generates at least one magnetic field that is detected by the at least one magnetoresistance sensor 88.

In an exemplary embodiment, the at least one magnetoresistance sensor 88 may be configured as a transmitter or magnetic field generator, and the at least one EM coil sensor 92 may be configured as a magnetic field receiver. It should, however, be appreciated that according to alternate embodiments the at least one magnetoresistance sensor 88 may be configured as a magnetic field receiver, and the at least one EM coil sensor 92 may be configured as a magnetic field generator.

In an exemplary embodiment, the at least one EM coil sensor 92 may be built with various EM coil architectures. In an exemplary embodiment, the EM coil sensor 92 may include single coils, a pair of single coils, single dipole coils, industry-standard-coil-architecture (ISCA) type coils, a pair of ISCA type coils, multiple coils, or an array of coils.

ISCA type coils are defined as three approximately collocated, approximately orthogonal, and approximately dipole coils. Therefore, ISCA coils include three approximately collocated, approximately orthogonal, and approximately dipole coils. In the ISCA configuration, the three coils (i.e., coil trios) exhibit the same effective area, are oriented orthogonally to one another, and are centered at the same point.

In an exemplary embodiment, the at least one EM coil sensor 92 may be configured from at least one EM microcoil that may be built with various EM microcoil architectures. In an exemplary embodiment, the EM microcoil may include a ferrite core with wire wound around the ferrite core. In an exemplary embodiment, the electromagnetic microcoil may include a ferrite material, such as a ferrite paste, that is applied to a plurality of projections with wire wound around the ferrite material. In an exemplary embodiment, each EM microcoil may be sealed within a shrinkwrap sleeve, coating, or shrinkable material on the outside of each microcoil.

The navigation interface 90 receives and/or transmits digitized signals from the at least one magnetoresistance sensor 88 or the at least one EM coil sensor 92. The digitized signals may be transmitted from the at least one magnetoresistance sensor 88 or the at least one EM coil sensor 92 to the navigation interface 90 using alternative wired or wireless communication protocols and interfaces.

The digitized signals received by the navigation interface 90 represent magnetic field information from the at least one magnetoresistance sensor 88 detected by the at least one EM coil sensor 92. In an alternative embodiment, the digitized signals received by the navigation interface 90 represent magnetic field information from the at least one EM coil sensor 92 detected by the at least one magnetoresistance sensor 88. The navigation interface 60 transmits the digitized signals to a tracker module 94 over a local interface 96. In an exemplary embodiment, the local interface 96 is a peripheral component interconnect (PCI) bus. In an exemplary embodiment, the tracker module 94 calculates position and orientation information based on the received digitized signals. This position and orientation information provides a location of a device. The tracker module 94 communicates the position and orientation information to a navigation module 98 over the local interface 96.

Upon receiving the position and orientation information, the navigation module 98 is used to register the location of the device to acquired patient data. The acquired patient data is stored on a disk 100. The acquired patient data may include computed tomography (CT) data, magnetic resonance (MR) data, positron emission tomography (PET) data, ultrasound data, x-ray data, or any other suitable data, as well as any combinations thereof. By way of example only, the disk 100 is a hard disk drive, but other suitable storage devices may be used.

The acquired patient data is loaded into memory 86 from the disk 100. The acquired patient data is retrieved from the disk 100 by a disk controller 102. The navigation module 98 reads from memory 86 the acquired patient data. The navigation module 98 registers the location of the device to acquired patient data, and generates image data suitable to visualize the patient image data and a representation of the device. The image data is transmitted to a display controller 104 over the local interface 96. The display controller 104 is used to output the image data to a display 106.

Figure 5:
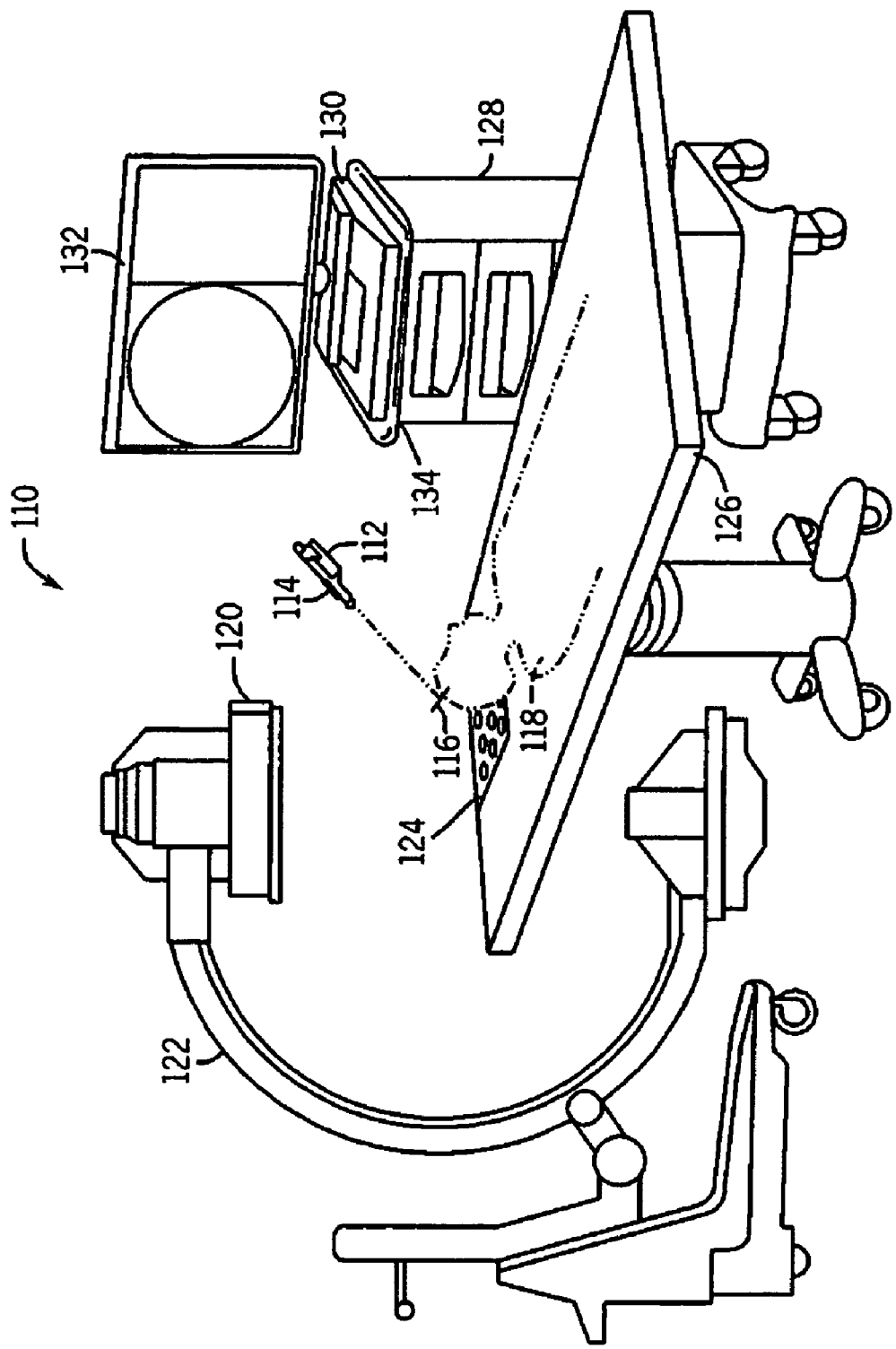
FIG. 5 is a schematic diagram of an exemplary embodiment of a surgical navigation system.

FIG. 5 illustrates a schematic diagram of an exemplary embodiment of a surgical navigation system 110. The surgical navigation system 110 includes at least one magnetoresistance sensor 112 attached to at least one device 114, a first magnetoresistance reference sensor 116 rigidly attached to an anatomical reference of a patient 118 undergoing a medical procedure, a second magnetoresistance reference sensor 120 attached to an imaging apparatus 122, a third magnetoresistance reference sensor 124 positioned on a table 126 supporting the patient 118, and a portable workstation 128. In an exemplary embodiment, the imaging apparatus 122 is a mobile fluoroscopic imaging apparatus. The portable workstation 128 includes a computer 130, at least one display 132, and a navigation interface 134. The surgical navigation system 110 is configured to operate with the at least one magnetoresistance sensor 112, the first, second and third magnetoresistance reference sensors 116, 120, 124 to determine the position and orientation of the at least one device 114.

The at least one magnetoresistance sensor 112 and the first, second and third magnetoresistance reference sensors 116, 120, 124 are coupled to the navigation interface 134. The at least one magnetoresistance sensor 112 and the first, second and third magnetoresistance reference sensors 116, 120, 124 may be coupled to and communicate to the navigation interface 134 through either a wired or wireless connection. The navigation interface is coupled to the computer 130.

The at least one magnetoresistance sensor 112 communicates with and transmits/receives data from the first, second and third magnetoresistance reference sensors 116, 120, 124. The navigation interface 134 is coupled to and receives data from the at least one magnetoresistance sensor 112 communicates with and transmits/receives data from the first, second and third magnetoresistance reference sensors 116, 120, 124. The surgical navigation system 110 provides the ability to track and display the position and orientation of multiple devices 114 having magnetoresistance sensors 112 attached thereto. The position and orientation information may be transmitted from the computer 130 to the display 132 for review by a medical practitioner.

In an exemplary embodiment, the at least one magnetoresistance sensor 112 and the first, second and third magnetoresistance reference sensors 116, 120, 124 may be configured as transmitters or magnetic field generator, or configured as magnetic field receivers, depending on the application.

The surgical navigation system 110 described herein is capable of tracking many different types of devices during different procedures. Depending on the procedure, the at least one device 114 may be a surgical instrument (e.g., an imaging catheter, a diagnostic catheter, a therapeutic catheter, a guidewire, a debrider, an aspirator, a handle, a guide, etc.), a surgical implant (e.g., an artificial disk, a bone screw, a shunt, a pedicle screw, a plate, an intramedullary rod, etc.), or some other device. Depending on the context of the usage of the surgical navigation system 110, any number of suitable devices may be used. In an exemplary embodiment, there may be more than one device 114, and more than one magnetoresistance sensor 112 attached to each device 114.

In an exemplary embodiment, a magnetoresistance reference sensor is fixed to an anatomical reference, a first magnetoresistance sensor is fixed to a first device or implant, and a second magnetoresistance sensor is fixed to a second device, implant or imaging apparatus.

In an exemplary embodiment, a magnetoresistance sensor is positioned on a surgical table, a magnetoresistance reference sensor is fixed to an anatomical reference, and a plurality of magnetoresistance sensors are fixed to devices, implants, patient body parts, and/or an imaging device.

In an exemplary embodiment, the at least one magnetoresistance sensor may be configured as a transmitter or magnetic field generator, and the at least one magnetoresistance reference sensor may be configured as a magnetic field receiver. It should, however, be appreciated that according to alternate embodiments the at least one magnetoresistance sensor may be configured as a magnetic field receiver, and the at least one magnetoresistance reference sensor may be configured as a magnetic field generator.

Figure 6:
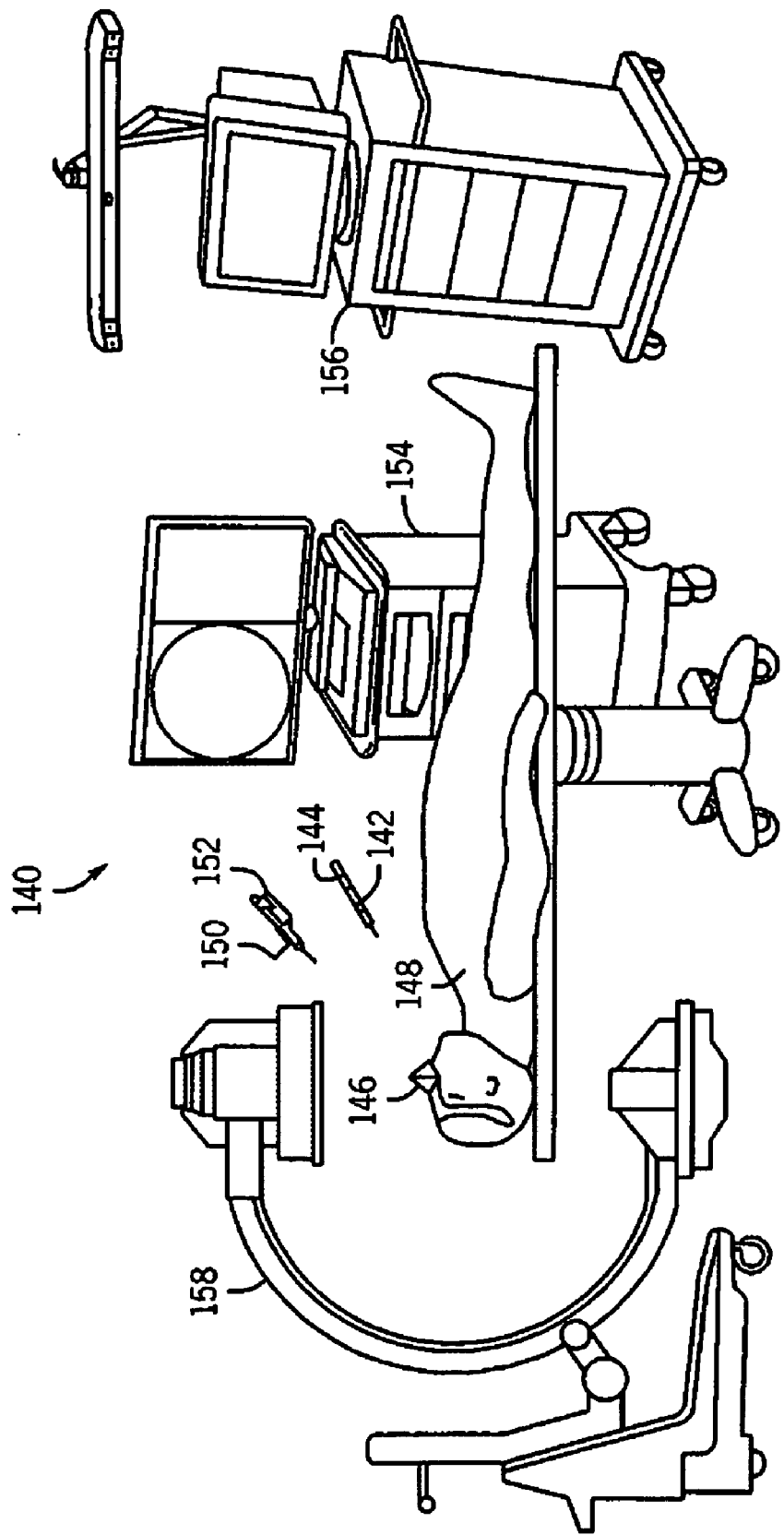
FIG. 6 is a schematic diagram of an exemplary embodiment of a surgical navigation system utilizing both optical and electromagnetic technologies.

FIG. 6 illustrates a schematic diagram of an exemplary embodiment of a surgical navigation system 140. The surgical navigation system 140 is a hybrid surgical navigation system implementing both EM and optical technologies. The surgical navigation system 140 includes at least one magnetoresistance sensor 142 attached to at least one device 144, a magnetoresistance reference sensor 146 rigidly attached to an anatomical reference of a patient 148 undergoing a medical procedure, at least one optical sensor 150 attached to at least one device 152, an imaging apparatus 158, a portable EM workstation 154, and an optical controller 156. In an exemplary embodiment, the imaging apparatus 158 is a mobile fluoroscopic imaging apparatus. The surgical navigation system 140 is configured to operate with the at least one magnetoresistance sensor 142, the magnetoresistance reference sensor 146, the at least one optical sensor 150 to determine the position and orientation of the at least one device 144 and the at least one device 152.

While the disclosure has been described with reference to various embodiments, those skilled in the art will appreciate that certain substitutions, alterations and omissions may be made to the embodiments without departing from the spirit of the disclosure. Accordingly, the foregoing description is meant to be exemplary only, and should not limit the scope of the disclosure as set forth in the following claims.

What is claimed is:

1. A surgical navigation system comprising:
   at least one magnetoresistance reference sensor coupled to a navigation interface and rigidly attachable to an anatomical reference of a patient;
   at least one magnetoresistance sensor coupled to the navigation interface and attachable to at least one device; and
   at least one processor coupled to the navigation interface for determining the position and orientation of the at least one device;
   wherein the at least one magnetoresistance reference sensor and the at least one magnetoresistance sensor each comprising:
      an insulating substrate;
      an alternating pattern of a metal material and a semiconductor material deposited on a surface of the insulating substrate; and
      a bias magnet material deposited on a surface of the alternating pattern of the metal material and the semiconductor material; and
   wherein the alternating pattern of the metal material and the semiconductor material is between the insulating substrate and the bias magnet material.

2. The surgical navigation system of claim 1, wherein the bias magnet material subjects the semiconductor material to a magnetic field.

3. The surgical navigation system of claim 2, wherein the magnetoresistance sensor provides a signal in response to a strength and a direction of the magnetic field.

4. The surgical navigation system of claim 1, wherein the magnetoresistance sensor has an active area of approximately 0.1 mm by 0.1 mm in size.

5. A surgical navigation system comprising:
   at least one magnetoresistance reference sensor rigidly attached to an anatomical reference of a patient;
   at least one electromagnetic coil sensor attached to at least one device; and
   at least one processor for determining the position and orientation of the at least one device;
   wherein the magnetoresistance reference sensor comprises an insulating substrate, an alternating pattern of a metal material and a semiconductor material deposited on a surface of the insulating substate, and a bias magnet material deposited on a surface of the alternating pattern of the metal material and the semiconductor material; and wherein the alternating pattern of the metal material and the semiconductor material is between the insulating substrate and the bias magnet material.

6. The surgical navigation system of claim 5, wherein the bias magnet material subjects the semiconductor material to a magnetic field.

7. The surgical navigation system of claim 6, wherein the magnetoresistance reference sensor provides a signal in response to a strength and a direction of the magnetic field.

8. The surgical navigation system of claim 7, wherein the magnetoresistance sensor has an active area of approximately 0.1 mm by 0.1 mm in size.

9. A surgical navigation system comprising:
at least one electromagnetic coil sensor rigidly attached to an anatomical reference of a patient;
at least one magnetoresistance sensor attached to at least one device; and
at least one processor for determining the position and orientation of the at least one device;
wherein the magnetoresistance sensor comprises an insulating substrate, an alternating pattern of a metal material and a semiconductor material deposited on a surface of the insulating substrate, and a bias magnet material deposited on a surface of the alternating pattern of the metal material and the semiconductor material; and
wherein the alternating pattern of the metal material and the semiconductor material is between the insulating substrate and the bias magnet material.

10. The surgical navigation system of claim 9, wherein the bias magnet material subjects the semiconductor material to a magnetic field.

11. The surgical navigation system of claim 10, wherein the magnetoresistance sensor provides a signal in response to a strength and a direction of the magnetic field.

12. The surgical navigation system of claim 9, wherein the magnetoresistance sensor has an active area of approximately 0.1 mm by 0.1 mm in size.

13. A surgical navigation system comprising:
at least one magnetoresistance reference sensor attachable to an anatomical reference of a patient;
at least one magnetoresistance sensor attachable to a first device;
at least one optical sensor attachable to a second device; and
at least one processor for determining the position and orientation of the first device and a second device;
wherein the magnetoresistance reference sensor comprises an insulating substrate, an alternating pattern of a metal material and a semiconductor material deposited on a surface of the insulating substrate, and a bias magnet material deposited on a surface of the alternating pattern of the metal material and the semiconductor material, and wherein the alternating pattern of the metal material and the semiconductor material is between the insulating substrate and the bias magnet material; and
wherein the magnetoresistance sensor comprises an insulating substrate, an alternating pattern of a metal material and a semiconductor material deposited on a surface of the insulating substrate, and a bias magnet material deposited on a surface of the alternating pattern of the metal material and the semiconductor material, and wherein the alternating pattern of the metal material and the semiconductor material is between the insulating substrate and the bias magnet material.

* * * * *